United States Patent
Steiner et al.

(10) Patent No.: US 10,758,500 B2
(45) Date of Patent: *Sep. 1, 2020

(54) TREATING ANDROGEN DEPRIVATION THERAPY INDUCED HOT FLASHES AND BONE LOSS IN MEN USING CIS-CLOMIPHENE

(71) Applicant: ASPEN PARK PHARMACEUTICALS, INC., Scarsdale, NY (US)

(72) Inventors: Mitchell Steiner, Germantown, TN (US); Harry Fisch, Scarsdale, NY (US)

(73) Assignee: ASPEN PARK PHARMACEUTICALS, INC., Scarsdale, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/580,198

(22) Filed: Sep. 24, 2019

(65) Prior Publication Data

US 2020/0085768 A1    Mar. 19, 2020

Related U.S. Application Data

(60) Continuation of application No. 15/879,861, filed on Jan. 25, 2018, now Pat. No. 10,463,635, which is a division of application No. 15/327,726, filed as application No. PCT/US2015/041761 on Jul. 23, 2015, now Pat. No. 9,913,815.

(60) Provisional application No. 62/028,540, filed on Jul. 24, 2014.

(51) Int. Cl.
*A61K 31/35*    (2006.01)
*A61K 31/138*    (2006.01)

(52) U.S. Cl.
CPC ................. *A61K 31/138* (2013.01)

(58) Field of Classification Search
CPC .................................................. A61K 31/135
USPC .......................................................... 514/649
See application file for complete search history.

(56) References Cited

U.S. PATENT DOCUMENTS

| 4,894,373 A | 1/1990 | Young |
| 9,913,815 B2 | 3/2018 | Steiner et al. |
| 10,463,635 B2 * | 11/2019 | Steiner ................. A61K 31/138 |
| 2004/0213841 A1 | 10/2004 | Steiner et al. |
| 2009/0215738 A1 | 8/2009 | Scally et al. |
| 2012/0157539 A1 | 6/2012 | Dalton et al. |

FOREIGN PATENT DOCUMENTS

| EP | 1574212 A1 | 9/2005 |
| WO | 03047504 A2 | 6/2003 |

OTHER PUBLICATIONS

Turner, Endocrinology, 139(9): 3712-3720 (1998).
Extended Search Report dated Nov. 24, 2017, in European Patent Application No. 15824708.0.
Szutu et al.; "Pharmacokinetics of intravenous clomiphene isomers"; Br. J. Clin. Pharmac., 1989, vol. 27, pp. 639-640.
International Search Report dated Oct. 26, 2015.
Ioannidou-Kadis, Fert. Steril., 86(5): 1-5 (2006).
"Clomid and Men," pp. 1-2, downloaded from website womenshealth.com, May 17, 2019.
"Clomid for Male Fertility," pp. 1, downloaded from website midwestreproductive.com, May 17, 2019.

* cited by examiner

*Primary Examiner* — Raymond J Henley, III
(74) *Attorney, Agent, or Firm* — Norris McLaughlin, P.A.

(57) ABSTRACT

This invention provides: 1) a method of treating androgen-deprivation induced osteoporosis, bone fractures, loss of bone mineral density (BMD), and/or hot flashes in a male subject suffering from prostate cancer; 2) a method of preventing androgen-deprivation induced osteoporosis, bone fractures, loss of bone mineral density (BMD), and/or hot flashes in a male subject suffering from prostate cancer; 3) a method of suppressing or inhibiting androgen-deprivation induced osteoporosis, bone fractures, loss of bone mineral density (BMD), and/or hot flashes in a male subject suffering from prostate cancer; and 4) a method of reducing the risk of developing androgen-deprivation induced osteoporosis, bone fractures, loss of bone mineral density (BMD), and/or hot flashes in a male subject suffering from prostate cancer, by administering to the subject a pharmaceutical composition comprising cis-clomiphene or a pharmaceutically acceptable salt thereof.

31 Claims, No Drawings

TREATING ANDROGEN DEPRIVATION THERAPY INDUCED HOT FLASHES AND BONE LOSS IN MEN USING CIS-CLOMIPHENE

This application is a continuation of U.S. application Ser. No. 15/879,861, filed Jan. 25, 2018, now allowed U.S. Pat. No. 10,463,635; which is a division of U.S. application Ser. No. 15/327,726, filed Jan. 20, 2017, now U.S. Pat. No. 9,913,815; which is a 371 of International Patent Application No. PCT/US15/41761, filed Jul. 23, 2015, which claims priority benefit of U.S. Provisional Application No. 62/028,540, filed Jul. 24, 2014, the disclosures of which patent applications are incorporated herein by reference.

BACKGROUND OF THE INVENTION

1. Field of the Invention

This invention relates to the prevention and treatment of androgen-deprivation induced osteoporosis, bone fractures and/or loss of bone mineral density (BMD) and hot flashes in men suffering from prostate cancer. More particularly, this invention relates to a method of treating, preventing, suppressing, inhibiting, or reducing the risk of developing androgen-deprivation induced osteoporosis, bone fractures and/or loss of BMD and hot flashes in men suffering from prostate cancer, comprising administering to a male subject suffering from prostate cancer cis-clomiphene or a pharmaceutically acceptable salt thereof.

2. Description of Related Art

Prostate cancer is one of the most frequently diagnosed noncutaneous cancers among men in the United States. One of the approaches to the treatment of prostate cancer is by androgen deprivation therapy (ADT). The male sex hormone, testosterone, stimulates the growth of cancerous prostatic cells and, therefore, is the primary fuel for the growth of prostate cancer. The goal of androgen deprivation is to decrease the stimulation by testosterone of the cancerous prostatic cells. Testosterone normally is produced by the testes in response to stimulation from a hormonal signal called luteinizing hormone (LH) which in turn is stimulated by luteinizing-hormone releasing hormone (LHRH). Androgen deprivation therapy is accomplished either surgically by bilateral orchiectomy or chemically by LHRH agonists or antagonists with or without nonsteroidal antiandrogens, like bicalutamide or enzalutamide, or lyase inhibitors like abiraterone.

Current studies suggest that early ADT in patients with micrometastatic disease may indeed prolong survival [Messing E M, et al (1999), *N Engl J Med* 34, 1781-1788; Newling (2001), *Urology* 58(*Suppl 2A*), 50-55]. Moreover, ADT is being employed in numerous new clinical settings, including neoadjuvant therapy prior to radical prostatectomy, long-term adjuvant therapy for patients at high risk for recurrence following radiation or surgery, neoadjuvant therapy for radiation, and treatment of biochemical recurrence following radiation or surgery [Carroll, et al (2001), *Urology* 58, 14; Horwitz E M, et al (2001), *Int J Radiat Oncol Biol Phy* March 15; 49(4), 947-56]. Thus, more prostate cancer patients have become candidates for and are being treated by ADT. Moreover, these prostate cancer patients are undergoing ADT earlier and longer than in the past, which in some cases may be as long as 10 or more years.

Unfortunately, ADT has significant adverse side effects, like hot flashes, osteoporosis, decreased lean muscle mass, depression and other mood changes, loss of libido, and erectile dysfunction [Stege R (2000), *Prostate Suppl* 10, 38-42]. Consequently, complications of ADT now contribute significantly to the morbidity, and in some cases the mortality, of men suffering from prostate cancer.

Hot flashes are characterized by the subjective sensation of a rise in temperature in the face and trunk and are accompanied by cutaneous vasodilatation predominantly in the face, throat and extremities, usually followed by profuse sweating. Following the administration of LHRH agonists or antagonists, the steep decline in serum luteinizing hormone and follicle stimulating hormone and rapid and sustained reductions in testosterone and estrogen blood levels results in the release of hypothalamic catecholamines, in particular norepinephrine. These flood the thermoregulation center in the upper hypothalamus, resulting in abnormal and poorly regulated peripheral vasodilatation and the occurrence of hot flushes and perspiration. (Khan et al. 2014, *Trends Urol. Men's Health* 5(1), 31-33).

It is estimated that up to 80 percent of patients on ADT will experience hot flashes and up to 27 percent of patients report them as their most troublesome side effect. Most patients will continue to experience these symptoms for as long as they are receiving ADT. Hot flashes can significantly impact on a patient's quality of life. Given that exposure to ADT may be lifelong in the palliative setting and may be two to three years in the adjuvant setting, there is a need to address all associated side effects and deal with them effectively in order to improve compliance with treatment and quality of life. (Reviewed in Khan 2014).

It is well established that the bone mineral density (BMD) of males decreases with age. Decreased amounts of bone mineral content and density correlates with decreased bone strength and predispose to fracture. The molecular mechanisms underlying the pleiotropic effects of sex-hormones in non-reproductive tissues are only beginning to be understood, but it is clear that physiologic concentrations of androgens and estrogens play an important role in maintaining bone homeostasis throughout the life-cycle. Consequently, when androgen or estrogen deprivation occurs, there is a resultant increase in the rate of bone remodeling that tilts the balance of resorption and formation in the favor of resorption, contributing to an overall loss of bone mass. In males, the natural decline in sex-hormones at maturity (direct decline in androgens as well as lower levels of estrogens derived from peripheral aromatization of androgens) is associated with the frailty of bones. Moreover, an important side effect in men suffering from prostate cancer undergoing ADT is the development of bone loss leading to osteoporosis and bone fractures. Loss of BMD occurs in the majority of patients being treated by ADT by 6 months.

New innovative approaches are urgently needed at both the basic science and clinical levels to decrease the incidence of androgen-deprivation induced hot flashes and bone loss and fractures in men suffering from prostate cancer on ADT.

SUMMARY OF THE INVENTION

In one embodiment, this invention provides a method of treating a subject suffering from a disorder selected from the group consisting of osteoporosis, bone fractures, loss of bone mineral density (BMD) and hot flashes, the method comprising the step of administering to said subject an effective amount therefor of a pharmaceutical composition comprising cis-clomiphene or a pharmaceutically acceptable salt thereof.

In one embodiment, this invention provides a method of treating a subject with hot flashes, the method comprising the step of administering to the subject cis-clomiphene or a pharmaceutically acceptable salt thereof.

In one embodiment, this invention provides a method of preventing hot flashes in a subject, the method comprising the step of administering to the subject cis-clomiphene or a pharmaceutically acceptable salt thereof.

In one embodiment, this invention provides a method of suppressing or inhibiting hot flashes in a subject, the method comprising the step of administering to the subject cis-clomiphene or a pharmaceutically acceptable salt thereof.

In one embodiment, this invention provides a method of reducing the risk of developing hot flashes in a subject, the method comprising the step of administering to the subject cis-clomiphene or a pharmaceutically acceptable salt thereof.

In one embodiment, the cis-clomiphene and/or the pharmaceutically acceptable salt thereof is administered at a daily dosage of about 5 mg. In another embodiment, the cis-clomiphene and/or the pharmaceutically acceptable salt thereof is administered at a daily dosage of about 15 mg. In another embodiment, the cis-clomiphene and/or the pharmaceutically acceptable salt thereof is administered at a daily dosage of about 25 mg. In another embodiment, the cis-clomiphene and/or the pharmaceutically acceptable salt thereof is administered at a daily dosage of about 50 mg.

The present invention provides a safe and effective method for treating, preventing, suppressing, inhibiting or reducing the risk of developing androgen-deprivation induced osteoporosis, bone fractures and/or loss of BMD and hot flashes and is particularly useful for treating male subjects suffering from prostate cancer having an elevated risk of developing androgen-deprivation induced osteoporosis, bone fractures and/or loss of BMD and hot flashes.

DETAILED DESCRIPTION OF THE INVENTION

This invention provides: 1) a method of treating a subject with hot flashes; 2) a method of preventing hot flashes in a subject; 3) a method of suppressing or inhibiting hot flashes in a subject; 4) a method of reducing the risk of developing hot flashes in a subject; 5) a method of treating androgen-deprivation induced osteoporosis in a male subject suffering from prostate cancer; 6) a method of preventing androgen-deprivation induced osteoporosis in a male subject suffering from prostate cancer; 7) a method of suppressing or inhibiting androgen-deprivation induced osteoporosis in a male subject suffering from prostate cancer; 8) a method of reducing the risk of developing androgen-deprivation induced osteoporosis in a male subject suffering from prostate cancer; 9) a method of treating androgen-deprivation induced loss of BMD in a male subject suffering from prostate cancer; 10) a method of preventing androgen-deprivation induced loss of BMD in a male subject suffering from prostate cancer; 11) a method of suppressing or inhibiting androgen-deprivation induced loss of BMD in a male subject suffering from prostate cancer; 12) a method of reducing the risk of developing androgen-deprivation induced loss of BMD in a male subject suffering from prostate cancer; 13) a method of treating androgen-deprivation induced bone fractures in a male subject suffering from prostate cancer; 14) a method of preventing androgen-deprivation induced bone fractures in a male subject suffering from prostate cancer; 15) a method of suppressing or inhibiting androgen-deprivation induced bone fractures in a male subject suffering from prostate cancer; 16) a method of reducing the risk of developing androgen-deprivation induced bone fractures in a male subject suffering from prostate cancer by administering to the subject cis-clomiphene or a pharmaceutically acceptable salt thereof.

Cis-clomiphene has the chemical structure:

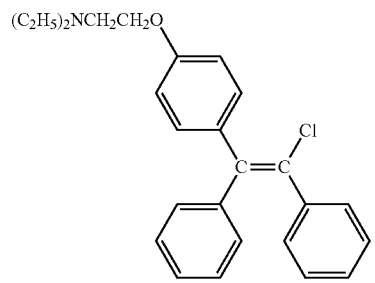

Cis-clomiphene (a.k.a. zuclomiphene)

Cis-clomiphene is currently marketed as a component of CLOMID®, which is a mixture of two enantiomers, trans-clomiphene and cis-clomiphene, in a ratio of trans:cis isomer ranging from about 50:50 to about 70:30. Cis-clomiphene is the more estrogenic isomer of the two. Substantially pure cis-clomiphene and the pharmaceutically acceptable salts thereof are already well known in the art (see, for example, U.S. Pat. No. 3,848,030, incorporated herein by reference) and, moreover, even were they not well known in the art methods by which they can be prepared are well known to and within the skill of the ordinary artisan. By "substantially pure" is meant cis-clomiphene containing less than 10% by weight, based on the total weight of the enantiomer mixture of trans-clomiphene, preferably less than 5%, more preferably less than 2%, most preferably not more than a trace of trans-clomiphene.

One of the important side effects of CLOMID® as listed in the package insert is hot flashes. Thus, CLOMID® does not treat hot flashes. An unexpected finding is that the cis-clomiphene isomer, the estrogenic isomer, can treat and prevent hot flashes and bone loss and fractures. The present methods contemplate the administration of cis-clomiphene or a pharmaceutically acceptable salt thereof.

In another embodiment, the present invention contemplates the administration of substantially pure clomiphene or a pharmaceutically acceptable salt thereof.

In another embodiment, the present invention contemplates the administration of clomiphene or a pharmaceutically acceptable salt thereof enriched in cis-clomiphene compared to CLOMID®. Thus, in this embodiment, the present invention contemplates the administration of clomiphene or a pharmaceutically acceptable salt thereof comprising both trans-isomer and cis-isomer in a ratio of trans:cis ranging from 49:51 to 0:100, preferably 25:75 to 0:100, most preferably 10:90 to 0:100.

In yet another embodiment, the present invention contemplates the administration of clomiphene or a pharmaceutically acceptable salt thereof comprising about 100% by weight of cis-clomiphene or a pharmaceutically acceptable salt thereof. In this context, "about 100% by weight of cis-clomiphene or a pharmaceutically acceptable salt thereof" means the composition administered comprises less than 2% by weight of trans-isomer, preferably not more than a trace amount of trans-isomer.

Various embodiments of dosage ranges are contemplated by this invention. In one embodiment, the dosage is in the range of 1-80 mg/day. In another embodiment, the dosage is in the range of 5-80 mg/day. In another embodiment the dosage is in the range of 35-66 mg/day. In another embodiment the dosage is in the range of 20-80 mg/day. In another embodiment the dosage is in the range of 20-60 mg/day. In another embodiment the dosage is in the range of 40-60 mg/day. In another embodiment the dosage is in a range of 45-60 mg/day. In another embodiment the dosage is in the range of 15-25 mg/day. In another embodiment the dosage is in the range of 55-65 mg/day. In one embodiment, the dosage is 5 mg/day. In another embodiment, the dosage is 15 mg/day. In another embodiment, the dosage is 25 mg/day. In another embodiment, the dosage is 50 mg/day.

Accordingly, in one embodiment, this invention provides a method of treating a subject with hot flashes, the method comprising the step of administering to the subject cis-clomiphene or a pharmaceutically acceptable salt thereof, at a dosage of about 5 mg to about 50 mg per day.

In one embodiment, this invention provides a method of preventing hot flashes in a subject, the method comprising the step of administering to the subject cis-clomiphene or a pharmaceutically acceptable salt thereof, at a dosage of about 5 mg to about 50 mg per day.

In one embodiment, this invention provides a method of suppressing or inhibiting hot flashes in a subject, the method comprising the step of administering to the subject cis-clomiphene or a pharmaceutically acceptable salt thereof, at a dosage of about 5 mg to about 50 mg per day.

In one embodiment, this invention provides a method of reducing the risk of developing hot flashes in a subject, the method comprising the step of administering to the subject cis-clomiphene or a pharmaceutically acceptable salt thereof, at a dosage of about 5 mg to about 50 mg per day.

In one embodiment, the cis-clomiphene or the pharmaceutically acceptable salt thereof is administered at a daily dosage of about 5 mg. In another embodiment, the cis-clomiphene or the pharmaceutically acceptable salt thereof is administered at a daily dosage of about 15 mg. In another embodiment, the cis-clomiphene or the pharmaceutically acceptable salt thereof is administered at a daily dosage of about 25 mg. In another embodiment, the cis-clomiphene or the pharmaceutically acceptable salt thereof is administered at a daily dosage of about 50 mg.

Hot flashes are caused by thermoregulatory dysfunction because of the low levels of testosterone and estrogen induced by ADT and is manifested by varying frequencies of sweating and chills that can be mild to severe in intensity. Moderate to severe hot flashes may cause the subject to not be able to continue normal daily activities. Hot flashes are one of the major reasons why patients become noncompliant with their anticancer, androgen deprivation therapy. Osteoporosis is a systemic skeletal disease, characterized by low bone mass and deterioration of bone tissue, with a consequent increase in bone fragility and susceptibility to fracture. In osteoporotic patients, bone strength is abnormal, with a resulting increase in the risk of fracture. Osteoporosis depletes both the calcium and the protein collagen normally found in the bone, resulting in either abnormal bone quality or decreased bone density. Bones that are affected by osteoporosis can fracture with only a minor fall or injury that normally would not cause a bone fracture. The fracture can be either in the form of cracking (as in a hip fracture) or collapsing (as in a compression fracture of the spine). The spine, hips, and wrists are common areas of osteoporosis bone fractures, although fractures can also occur in other skeletal areas.

Bone mineral density is a measured calculation of the true mass of bone. The absolute amount of bone as measured by BMD generally correlates with bone strength and its ability to bear weight. By measuring BMD, it is possible to predict fracture risk in the same manner that measuring blood pressure can help predict the risk of stroke.

Bone mineral density in one embodiment can be measured by known bone-mineral content mapping techniques. Bone density of the hip, spine, wrist, or calcaneus may be measured by a variety of techniques. The preferred method of BMD measurement is dual-energy x-ray densitometry (DXA). Bone mineral density of the hip, antero-posterior spine, lateral spine, and wrist can be measured using this technology. Measurement at any site predicts overall risk of fracture, but information from a specific site is the best predictor of fracture at that site. Quantitative computerized tomography is also used to measure BMD of the spine. See for example, "Nuclear Medicine: "Quantitative Procedures", by Wahner H W, Dunn W L, Thorsen H C, et al, published by Toronto Little, Brown & Co., 1983, (see pages 107-132). An article entitled "Assessment of Bone Mineral Part 1" appeared in the *Journal of Nuclear Medicine*, pp 1134-1141, (1984). Another article entitled "Bone Mineral Density of The Radius" appeared in Vol. 26, No. 11, (1985) November *Journal of Nuclear Medicine* at pp 13-39. Abstracts on the use of gamma cameras for bone-mineral content measurements are (a) S. Hoory et al, *Radiology*, Vol. 157(P), p. 87 (1985), and (b) C. R. Wilson et al, *Radiology*, Vol. 157(P), p. 88 (1985).

The present invention provides a safe and effective method for treating, preventing, suppressing, inhibiting or reducing the risk of developing androgen-deprivation induced osteoporosis and/or loss of BMD and is particularly useful for treating male subjects suffering from prostate cancer having an elevated moderate to severe hot flashes induced by risk of developing androgen-deprivation induced osteoporosis. In one embodiment, the male subject is a mammalian subject. In another embodiment, the male subject is a human subject.

Furthermore, the anti-estrogens presented herein cis-clomiphene and the pharmaceutically acceptable salts thereof are effective at treating, suppressing or inhibiting osteopenia accompanied by bone loss. "Osteopenia" refers to decreased calcification or density of bone. This is a term which encompasses all skeletal systems in which such a condition is noted.

As contemplated herein, the present invention relates to the use of cis-clomiphene or a pharmaceutically acceptable salt thereof for treating, preventing, suppressing, inhibiting or reducing the risk of developing androgen-deprivation induced osteoporosis and/or loss of BMD at a dosage of about 5 mg to about 50 mg per day. Thus, in one embodiment, the methods of the present invention comprise administering cis-clomiphene. In another embodiment, the methods of the present invention comprise administering a pharmaceutically acceptable salt of the cis-clomiphene.

The invention includes "pharmaceutically acceptable salts" of the amino-substituted compound with organic and inorganic acids, for example, citric acid and hydrochloric acid. The invention also includes N-oxides of the amino substituent.

Pharmaceutical Compositions

In one embodiment, the methods of the present invention comprise administering a pharmaceutical composition comprising the cis-clomiphene or a pharmaceutically acceptable salt thereof; and a pharmaceutically acceptable carrier. The pharmaceutical composition is administered to a male subject suffering from prostate cancer; for treating and/or preventing androgen-deprivation induced osteoporosis and/or loss of BMD; for suppressing or inhibiting androgen-deprivation induced osteoporosis and/or loss of BMD; and/or for reducing the risk of developing androgen-deprivation induced osteoporosis and/or loss of BMD in the male subject.

As used herein, "pharmaceutical composition" means a "therapeutically effective amount" of the active ingredient, i.e. the cis-clomiphene and/or pharmaceutically acceptable salt thereof, together with a pharmaceutically acceptable carrier or diluent. A "therapeutically effective amount" as used herein refers to that amount which provides a therapeutic effect for a given condition and administration regimen.

The pharmaceutical compositions containing the cis-clomiphene or a pharmaceutically acceptable salt thereof can be administered to a subject by any method known to a person skilled in the art, such as parenterally, parancancerally, transmucosally, transdermally, intramuscularly, intravenously, intradermally, subcutaneously, intraperitonealy, intraventricularly, intracranially, intravaginally or intratumorally.

In one embodiment, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In one embodiment of the present invention, the cis-clomiphene and/or pharmaceutically acceptable salt thereof are formulated in a capsule. In accordance with this embodiment, the compositions of the present invention comprise, in addition to the cis-clomiphene and/or pharmaceutically acceptable salt thereof active compound and the inert carrier or diluent, a hard gelating capsule.

Further, in another embodiment, the pharmaceutical compositions are administered by intravenous, intraarterial, intranasal, or intramuscular injection of a liquid preparation. Suitable liquid formulations include solutions, suspensions, dispersions, emulsions, oils and the like. In one embodiment, the pharmaceutical compositions are administered intravenously, and are thus formulated in a form suitable for intravenous administration. In another embodiment, the pharmaceutical compositions are administered intraarterially, and are thus formulated in a form suitable for intraarterial administration. In another embodiment, the pharmaceutical compositions are administered intramuscularly, and are thus formulated in a form suitable for intramuscular administration.

Further, in another embodiment, the pharmaceutical compositions are administered topically to body surfaces, and are thus formulated in a form suitable for topical administration. Suitable topical formulations include gels, ointments, creams, lotions, drops and the like. For topical administration, the cis-clomiphene and/or pharmaceutically acceptable salt thereof are prepared and applied as solutions, suspensions, or emulsions in a physiologically acceptable diluent with or without a pharmaceutical carrier.

Further, in another embodiment, the pharmaceutical compositions are administered as a suppository, for example a rectal suppository or a urethral suppository. Further, in another embodiment, the pharmaceutical compositions are administered by subcutaneous implantation of a pellet. In a further embodiment, the pellet provides for controlled release of cis-clomiphene or pharmaceutically acceptable salt thereof over a period of time.

In another embodiment, the active compound can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid).

As used herein "pharmaceutically acceptable carriers or diluents" are well known to those skilled in the art. The carrier or diluent may be a solid carrier or diluent for solid formulations, a liquid carrier or diluent for liquid formulations, or mixtures thereof.

Solid carriers/diluents include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil.

Parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of petroleum, animal, vegetable, or synthetic origin, for example, peanut oil, soybean oil, mineral oil, olive oil, sunflower oil, and fish-liver oil.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hydroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

In one embodiment, the pharmaceutical compositions provided herein are controlled-release compositions, i.e. compositions in which the cis-clomiphene and/or the pharmaceutically acceptable salt thereof is released over a period of time after administration. Controlled- or sustained-release compositions include formulation in lipophilic depots (e.g. fatty acids, waxes, oils). In another embodiment, the composition is an immediate-release composition, i.e. a composition in which all of the cis-clomiphene or pharmaceutically acceptable salt thereof is released immediately after administration.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, *CRC Crit. Ref. Biomed. Eng.* 14:201 (1987); Buchwald et al., *Surgery* 88:507 (1980); Saudek et al., *N. Engl. J. Med.* 321: 574 (1989). In another embodiment, polymeric materials can be used. In yet another embodiment, a controlled release system can be placed in proximity to the therapeutic target, i.e., the brain, thus requiring only a fraction of the systemic dose (see, e.g., Goodson, in *Medical Applications of Controlled Release*, supra, vol. 2, pp. 115-138 (1984). Other controlled-release systems are discussed in the review by Langer (*Science* 249:1527-1533 (1990).

The compositions may also include incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound abducts less frequently or in lower doses than with the unmodified compound.

The preparation of pharmaceutical compositions which contain an active component is well understood in the art, for example by mixing, granulating, or tablet-forming processes. The active therapeutic ingredient is often mixed with excipients which are pharmaceutically acceptable and compatible with the active ingredient. For oral administration, the cis-clomiphene and/or pharmaceutically acceptable salt thereof are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the cis-clomiphene and/or pharmaceutically acceptable salt thereof are converted into a solution, suspension, or emulsion, if desired with the substances customary and suitable for this purpose, for example, solubilizers or other.

An active component can be formulated into the composition as neutralized pharmaceutically acceptable salt forms. Pharmaceutically acceptable salts include the acid addition salts (formed with the amino group of the molecule), which are formed with inorganic acids such as, for example, hydrochloric or phosphoric acids, or such organic acids as acetic, oxalic, tartaric, mandelic, and the like.

For use in medicine, the salts of the cis-clomiphene are pharmaceutically acceptable salts. Other salts may, however, be useful in the preparation of the compounds according to the invention or of their pharmaceutically acceptable salts. Suitable pharmaceutically acceptable salts of the compounds of this invention include acid addition salts which may, for example, be formed by mixing a solution of the compound according to the invention with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid or phosphoric acid.

In another embodiment, the term "contacting" means that the cis-clomiphene and/or pharmaceutically acceptable salt thereof of the present invention is introduced into a subject receiving treatment, and the cis-clomiphene and/or pharmaceutically acceptable salt thereof is allowed to come in contact with the androgen receptor in vivo.

As used herein, the term "treating" includes preventative as well as disorder remitative treatment. As used herein, the terms "reducing", "suppressing" and "inhibiting" have their commonly understood meaning of lessening or decreasing. As used herein, the term "progression" means increasing in scope or severity, advancing, growing or becoming worse. As used herein, the term "recurrence" means the return of a disease after a remission.

As used herein, the term "administering" refers to bringing a subject in contact with the cis-clomiphene and/or pharmaceutically acceptable salt thereof of the present invention. As used herein, administration can be accomplished in vitro, i.e. in a test tube, or in vivo, i.e. in cells or tissues of living organisms, for example humans. In one embodiment, the present invention encompasses administering the compounds of the present invention to a subject.

In one embodiment, the methods of the present invention comprise administering the cis-clomiphene and/or pharmaceutically acceptable salt thereof as the sole active ingredient. However, also encompassed within the scope of the present invention are methods for hormone therapy, for treating prostate cancer, for delaying the progression of prostate cancer, and for preventing and/or treating the recurrence of prostate cancer, which comprise administering the cis-clomiphene and/or pharmaceutically acceptable salt thereof in combination with one or more therapeutic agents. These agents include, but are not limited to: LHRH agonists, LHRH antagonists, reversible antiandrogens (such as bicalutamide, flutamide, enzalutamide, and ARN-509), lyase inhibitors (abiraterone), other anti-estrogens, anticancer drugs, 5-alpha reductase inhibitors, aromatase inhibitors, progestins, selective androgen receptor modulators (SARMS) or agents acting through other nuclear hormone receptors.

Thus, in one embodiment, the methods of the present invention include using compositions and pharmaceutical compositions comprising cis-clomiphene and/or pharmaceutically acceptable salt thereof in combination with an LHRH agonist or antagonist. In another embodiment, the methods of the present invention include using compositions and pharmaceutical compositions comprising cis-clomiphene and/or pharmaceutically acceptable salt thereof in combination with a reversible antiandrogen. In another embodiment, the methods of the present invention include using compositions and pharmaceutical compositions comprising cis-clomiphene and/or pharmaceutically acceptable salt thereof in combination with an anti-estrogen. In another embodiment, the methods of the present invention include using compositions and pharmaceutical compositions comprising cis-clomiphene and/or pharmaceutically acceptable salt thereof in combination with an anticancer drug. In another embodiment, the methods of the present invention include using compositions and pharmaceutical compositions comprising cis-clomiphene and/or pharmaceutically acceptable salt thereof in combination with a 5-alpha reductase inhibitor. In another embodiment, the methods of the present invention include using compositions and pharmaceutical compositions comprising cis-clomiphene and/or pharmaceutically acceptable salt thereof in combination with an aromatase inhibitor. In another embodiment, the methods of the present invention include using compositions and pharmaceutical compositions comprising cis-clomiphene and/or pharmaceutically acceptable salt thereof in combination with a progestin. In another embodiment, the methods of the present invention include using compositions and pharmaceutical compositions comprising cis-clomiphene and/or pharmaceutically acceptable salt thereof in combination with a SARM. In another embodiment, the methods of the present invention include using compositions and pharmaceutical compositions comprising cis-clomiphene and/or pharmaceutically acceptable salt thereof in combination with an agent acting through other nuclear hormone receptors.

A pharmaceutically effective dosage of the cis-clomiphene or pharmaceutically acceptable salt thereof is administered to the patients for an effective time period, preferably, for 2 years and most preferably continuously (for the remainder of the patient's life). For example, at a daily dose of 5-10 mg once or twice a day, cis-clomiphene or pharmaceutically acceptable salt thereof is administered to obtain a target reduction in the frequency of hot flashes and can thus give an indication of whether dose adjustment should be undertaken.

The following examples are presented in order to more fully illustrate the preferred embodiments of the invention. They should in no way, however, be construed as limiting the broad scope of the invention.

EXAMPLES

Example 1: Treatment of Hot Flashes

Due to the deleterious effects of testosterone on prostate cancer, the gold standard treatment for advanced prostate cancer is surgical or chemical castration of the patient. However, the resulting low testosterone and estrogen levels can have significant side effects including loss of bone leading to osteoporosis, and fractures as well as hot flashes. The adverse effect of hot flashes is primarily a quality of life issue. However, hot flashes are often cited as the number one reason for the lack of compliance with anticancer therapy including ADT in these men.

Men suffering from hot flashes who have advanced prostate cancer on ADT are given daily doses of 25 mg of cis-clomiphene citrate (about 100% cis-isomer) for a period of at least three months. Assessments are made as to the frequency and severity of hot flashes at baseline and after three months of treatment.

Example 2: Effect of Cis-Clomiphene on Bone Turnover

Men who have advance prostate cancer on ADT are treated with 50 mg/d of substantially cis-clomiphene for 6 months. At Day 180, baseline bone turnover markers like serum bone specific alkaline phosphatase and are compared to current values as well as BMD by DEXA. The expectation is that cis-clomiphene shows estrogenic effects on bone favorably affecting bone turnover markers and BMD in men.

Bone analysis methodology may be carried out as described in U.S. Patent Publication No. 2004/0214898, the pertinent contents of which are incorporated herein by reference.

It will be appreciated by a person skilled in the art that the present invention is not limited by what has been particularly shown and described hereinabove. Rather, the scope of the invention is defined by the claims which follow:

What is claimed is:

1. A method of treating loss of bone mineral density (BMD) in a male subject suffering therefrom, said method comprising the step of orally administering to said male subject an effective amount therefor of a pharmaceutical composition comprising (A) cis-clomiphene or a pharmaceutically acceptable salt thereof and (B) less than 10% by weight of trans-clomiphene or a pharmaceutically acceptable salt thereof, wherein said less than 10% by weight is based on a total weight of (A)+(B).

2. The method according to claim 1, wherein said pharmaceutical composition is a pellet, a tablet, a capsule, a solution, a suspension, an emulsion, an elixir, or a gel.

3. A method of suppressing, inhibiting or reducing the risk of loss of bone mineral density to a male subject undergoing androgen-deprivation therapy, said method comprising the step of orally administering to said male subject an effective amount therefor of a pharmaceutical composition comprising (A) cis-clomiphene or a pharmaceutically acceptable salt thereof and (B) less than 10% by weight of trans-clomiphene or a pharmaceutically acceptable salt thereof, wherein said less than 10% by weight is based on a total weight of (A)+(B).

4. The method according to claim 3, wherein said pharmaceutical composition is a pellet, a tablet, a capsule, a solution, a suspension, an emulsion, an elixir, or a gel.

5. The method according to claim 1, wherein the pharmaceutical composition comprises less than 5% by weight of trans-clomiphene or a pharmaceutically acceptable salt thereof, wherein said less than 5% by weight is based on a total weight of (A)+(B).

6. The method according to claim 5, wherein the pharmaceutical composition comprises less than 2% by weight of trans-clomiphene or a pharmaceutically acceptable salt thereof, wherein said less than 2% by weight is based on a total weight of (A)+(B).

7. The method according to claim 6, wherein said pharmaceutical composition is a tablet.

8. The method according to claim 7, wherein the cis-clomiphene or pharmaceutically acceptable salt thereof is cis-clomiphene citrate.

9. The method according to claim 6, wherein said pharmaceutical composition is a hard or soft gelatin capsule.

10. The method according to claim 9, wherein the cis-clomiphene or pharmaceutically acceptable salt thereof is cis-clomiphene citrate.

11. The method according to claim 1, wherein the pharmaceutical composition further comprises at least one additional therapeutic agent selected from the group consisting of luteinizing-hormone releasing hormone (LHRH) agonists and antagonists.

12. The method according to claim 1, wherein the male additionally suffers from osteoporosis and/or bone fractures.

13. The method according to claim 3, wherein the pharmaceutical composition comprises less than 5% by weight of trans-clomiphene or a pharmaceutically acceptable salt thereof, wherein said less than 5% by weight is based on a total weight of (A)+(B).

14. The method according to claim 13, wherein the pharmaceutical composition comprises less than 2% by weight of trans-clomiphene or a pharmaceutically acceptable salt thereof, wherein said less than 2% by weight is based on a total weight of (A)+(B).

15. The method according to claim 14, wherein said pharmaceutical composition is a tablet.

16. The method according to claim 15, wherein the cis-clomiphene or pharmaceutically acceptable salt thereof is cis-clomiphene citrate.

17. The method according to claim 14, wherein said pharmaceutical composition is a hard or soft gelatin capsule.

18. The method according to claim 17, wherein the cis-clomiphene or pharmaceutically acceptable salt thereof is cis-clomiphene citrate.

19. The method according to claim 3, wherein the pharmaceutical composition further comprises at least one additional therapeutic agent selected from the group consisting of luteinizing-hormone releasing hormone (LHRH) agonists and antagonists.

20. The method according to claim 3, wherein the male additionally suffers from osteoporosis and/or bone fractures.

21. A method of suppressing or inhibiting loss of bone mineral density in a male patient undergoing androgen deprivation therapy for the treatment of prostate cancer, said method comprising the step of orally administering to said subject an effective amount therefor of a pharmaceutical composition comprising (A) cis-clomiphene or a pharmaceutically acceptable salt thereof and (B) less than 10% by weight of trans-clomiphene or a pharmaceutically acceptable salt thereof, wherein said less than 10% by weight is based on a total weight of (A)+(B).

22. The method according to claim 21, wherein the male additionally suffers from osteoporosis and/or bone fractures.

23. The method according to claim 21, wherein the pharmaceutical composition further comprises at least one additional therapeutic agent selected from the group consisting of luteinizing-hormone releasing hormone (LHRH) agonists and antagonists.

24. The method according to claim 21, wherein the pharmaceutical composition comprises less than 5% by weight of trans-clomiphene or a pharmaceutically acceptable salt thereof, wherein said less than 5% by weight is based on a total weight of (A)+(B).

25. The method according to claim 24, wherein the pharmaceutical composition comprises less than 2% by weight of trans-clomiphene or a pharmaceutically acceptable salt thereof, wherein said less than 2% by weight is based on a total weight of (A)+(B).

26. The method according to claim 25, wherein said pharmaceutical composition is a tablet.

27. The method according to claim 26, wherein the cis-clomiphene or pharmaceutically acceptable salt thereof is cis-clomiphene citrate.

28. The method according to claim 25, wherein said pharmaceutical composition is a hard or soft gelatin capsule.

29. The method according to claim 28, wherein the cis-clomiphene or pharmaceutically acceptable salt thereof is cis-clomiphene citrate.

30. The method according to claim 21, which comprises orally administering to said male said pharmaceutical composition comprising less than 5% by weight of trans-clomiphene or a pharmaceutically acceptable salt thereof, wherein said less than 5% by weight is based on the total weight of (A)+(B), wherein said administering is optionally along with at least one additional therapeutic agent selected from the group consisting of luteinizing-hormone releasing hormone (LHRH) agonists and antagonists, wherein optionally the male additionally suffers from osteoporosis and/or bone fractures.

31. The method according to claim 30, wherein the pharmaceutical composition comprises less than 2% by weight of trans-clomiphene or a pharmaceutically acceptable salt thereof, wherein said less than 2% by weight is based on a total weight of (A)+(B).

* * * * *